(12) United States Patent
Aubart et al.

(10) Patent No.: US 7,332,485 B2
(45) Date of Patent: Feb. 19, 2008

(54) PEPTIDE DEFORMYLASE INHIBITORS

(75) Inventors: Kelly M. Aubart, Collegeville, PA (US); Siegfried Benjamin Christensen, IV, Collegeville, PA (US); Chaya Duraiswami, Collegeville, PA (US); Joseph M. Karpinski, Collegeville, PA (US)

(73) Assignee: SmithKline Beecham Corp, Philadelphia, PA (US)

( * ) Notice: Subject to any disclaimer, the term of this patent is extended or adjusted under 35 U.S.C. 154(b) by 3 days.

(21) Appl. No.: 10/563,777

(22) PCT Filed: Jul. 8, 2004

(86) PCT No.: PCT/US2004/022067

§ 371 (c)(1),
(2), (4) Date: Jan. 6, 2006

(87) PCT Pub. No.: WO2005/005456

PCT Pub. Date: Jan. 20, 2005

(65) Prior Publication Data

US 2006/0160802 A1    Jul. 20, 2006

Related U.S. Application Data

(60) Provisional application No. 60/485,510, filed on Jul. 8, 2003.

(51) Int. Cl.
*C07D 239/42* (2006.01)
*C07D 251/72* (2006.01)
*C07D 263/30* (2006.01)
*C07D 307/08* (2006.01)
*A61K 31/505* (2006.01)
*A61K 31/506* (2006.01)
*A61P 31/04* (2006.01)
*A61K 31/53* (2006.01)
*A61K 31/16* (2006.01)
*A61K 31/5377* (2006.01)

(52) U.S. Cl. .................. 514/231.5; 514/243; 514/275; 514/462; 514/613; 514/614; 544/111; 544/183; 544/330; 549/462; 564/159; 564/160

(58) Field of Classification Search ................ 564/159, 564/160; 544/111, 183, 330; 549/462; 514/613, 514/614, 231.5, 243, 275, 462
See application file for complete search history.

(56) References Cited

U.S. PATENT DOCUMENTS

| | | |
|---|---|---|
| 6,455,502 B1 | 9/2002 | Bryant et al. .................. 514/19 |
| 7,019,003 B2 | 3/2006 | Xiang et al. |
| 2005/0222412 A1 | 10/2005 | Aubart et al. |

OTHER PUBLICATIONS

Snyder et al., J. Med. Liban 48(4): 208-214, 2000.*

* cited by examiner

*Primary Examiner*—Venkataraman Balasubramanian
(74) *Attorney, Agent, or Firm*—Laura K. Madden; Loretta Sauermelch; Mary E. McCarthy

(57) ABSTRACT

Novel PDF inhibitors and novel methods for their use are provided.

3 Claims, No Drawings

PEPTIDE DEFORMYLASE INHIBITORS

This application is a 371 of International Application Number PCT/US2004/022067, filed 08 Jul. 2004, which claims priority of U.S. Provisional Application No. 60/485,510, filed 08 Jul. 2003.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

FIG. 1.
The methionine cycle.

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165-168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749-761, 1997).

PDF is recognized to be an attractive antibacterial target, as this enzyme has been demonstrated to be essential for bacterial growth in vitro (Mazel, D. et al., EMBO J. 13 (4), 914-923, 1994), is not believed to be involved in eukaryotic protein synthesis (Rajagopalan et al., J. Am. Chem. Soc. 119, 12418-12419, 1997), and is universally conserved in prokaryotes (Kozak, M., Microbiol. Rev. 47, 1-45, 1983). Therefore PDF inhibitors can potentially serve as broad spectrum antibacterial agents.

SUMMARY OF THE INVENTION

The present invention involves novel antibacterial compounds represented by Formula (1) hereinbelow and their use as PDF inhibitors.

DETAILED DESCRIPTION OF THE INVENTION

In one aspect of the present invention, there is provided a compound of formula (1):

wherein:
A represents an optionally substituted carbocycle of 3 to 8 membered ring;
Y represents a bond except where X is a carbonyl wherein Y is a bond or $CH_2$;
X represents a carbonyl, $CH_2$ or a bond; and
R represents aryl or heteroaryl.

In this invention the most preferred absolute configuration of compounds of the formula (1) is indicated below:

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "substituted alkyl" refers to a straight or branched chain saturated hydrocarbon radical, optionally substituted with substituents selected from the group that includes $C_{1-3}$ alkyl (optionally substituted by one to three fluorines), $C_{2-3}$ alkenyl, $C_{2-3}$ alkynyl, $C_{1-2}$ alkoxy (optionally substituted by one to three fluorines), sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen, multiple degrees of substitution being allowed.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, optionally substituted with substituents selected from the group which includes $C_{1-3}$ alkyl (optionally substituted by one to three F), amino, aryl, cyano and halogen, multiple degrees of substitution being allowed.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally substituted with substituents selected from the group which includes $C_{1-3}$ alkyl (optionally substituted by one to three F), amino, aryl and halogen, multiple degrees of substitution being allowed.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical having from three to seven carbon atoms, and which is optionally substituted with substituents selected from the group which includes $C_{1-3}$ alkyl (optionally substituted by one to three F), $C_{2-3}$ alkenyl, $C_{2-3}$ alkynyl, $C_{1-2}$ alkoxy (optionally substituted by one to three F), sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen, multiple degrees of substitution being allowed. For carbocycles with five- to seven-membered rings, a ring double bond is allowed.

As used herein, the term "aryl" refers to an optionally substituted benzene ring or to an optionally substituted benzene ring fused to one or more optionally substituted benzene rings to form a ring system. Exemplary optional substituents include $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring or ring system may be optionally fused to one or more optionally substituted aryl rings (including benzene rings), carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six membered aromatic ring containing one or more heteroatomic substitutions selected from S, SO, $SO_2$, O, N, or N-oxide, or to such an aromatic ring fused to one or more optionally substituted rings, such as heteroaryl rings, aryl rings, heterocyclic rings, or carbocycle rings (e.g., a bicyclic or tricyclic ring system). Examples of optional substituents are selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido, multiple degrees of substitution being allowed. Examples of "heteroaryl" groups used herein include, but are not limited to, benzoimidazolyl, benzothiazolyl, benzoisothiazolyl, benzothiophenyl, benzopyrazinyl, benzotriazolyl, benzotriazinyl, benzo[1,4]dioxanyl, benzofuranyl, 9H-α-carbolinyl, cinnolinyl, 2,3-dihydro-[1,4]dioxino[2,3-b]-pyridinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrazolopyridinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein the term "aralkoxy" refers to the group —$OR_aR_b$, where $R_a$ is alkyl and $R_b$ is aryl as defined above.

As used herein the term "aryloxy" refers to the group —$OR_a$, where $R_a$ is aryl as defined above.

As used herein, the term "mercapto" refers to the group —SH.

As used herein, the term "sulfanyl" refers to the group —$SR_a$, where $R_a$ is substituted alkyl, substituted carbocycle, aryl, heteroaryl or heterocyclic, as defined above.

As used herein, the term "sulfinyl" refers to the group —$S(O)R_a$, where $R_a$ is substituted alkyl, substituted carbocycle, aryl, heteroaryl or heterocyclic, as defined above.

As used herein, the term "sulfonyl" refers to the group —$S(O)_2R_a$, where $R_a$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_a$ where $R_a$ is substituted alkyl, substituted carbocycle, aryl, heteroaryl or heterocyclic, as defined above.

As used herein, the term "carboxyamide" refers to the group —$NHC(O)R_a$ where $R_a$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_a$ wherein R$_a$ is hydrogen, alkyl, carbocycle or aryl as defined above.

As used herein, the term "guanidino" refers to the group —NHC(=NH)NH$_2$.

As used herein, the term "acyl" refers to the group —C(O)R$_a$, where R$_a$ is alkyl, carbocycle, or heterocyclic as defined herein.

As used herein, the term "aroyl" refers to the group —C(O)R$_a$, where R$_a$ is aryl as defined herein.

As used herein, the term "heteroaroyl" refers to the group —C(O)R$_a$, where R$_a$ is heteroaryl as defined herein.

As used herein, the term "acyloxy" refers to the group —OC(O)R$_a$, where R$_a$ is alkyl, carbocycle, or heterocyclic as defined herein.

As used herein, the term "aroyloxy" refers to the group —OC(O)R$_a$, where R$_a$ is aryl as defined herein.

As used herein, the term "heteroaroyloxy" refers to the group —OC(O)R$_a$, where R$_a$ is heteroaryl as defined herein.

Also included in the present invention are pharmaceutically acceptable salts and complexes, such as the hydrochloride, hydrobromide and trifluoroacetate salts and the sodium, potassium and magnesium salts. The compounds of the present invention may contain one or more asymmetric carbon atoms and may exist in racemic and optically active forms. All of these compounds and diastereomers are contemplated to be within the scope of the present invention.

Compounds useful in the present invention are selected from the group consisting of:
N-Hydroxy-N-{1-[N'-(4-trifluoromethyl-pyrimidin-2-yl)-hydrazinocarbonyl]-cyclopentylmethyl}-formamide
N-Hydroxy-N-{1-[N'-(7-methoxy-benzofuran-2-carbonyl)-hydrazinocarbonyl]-cyclopentylmethyl}-formamide
N-Hydroxy-N-{1-[N'-(4-trifluoromethyl-pyrimidin-2-yl)-hydrazinocarbonyl]-cyclohexylmethyl}-formamide
N-Hydroxy-N-{1-[N'-(7-methoxy-benzofuran-2-carbonyl)-hydrazinocarbonyl]-cyclohexylmethyl}-formamide
N-Hydroxy-N-{1-[N'-(5-methoxy-benzo[1,2,4triazin-3-yl)-hydrazinocarbonyl]-cyclohexylmethyl}-formamide
N-Hydroxy-N-{1-[N'-(7-methyl-benzo[1,2,4triazin-3-yl)-hydrazinocarbonyl]-cyclohexylmethyl}-formamide
N-{4,4-Dimethyl-1-[N'-(4-trifluoromethyl-pyrimidin-2-yl)-hydrazinocarbonyl]-cyclohexylmethyl}-N-hydroxy-formamide
N-{4,4-Dimethyl-1-[N'-(4-methyl-pyrimidin-2-yl)-hydrazinocarbonyl]-cyclohexylmethyl}-N-hydroxy-formamide
N-{4,4-Dimethyl-1-[N'-(4-methyl-6-morpholin-4-yl-pyrimidin-2-yl)-hydrazinocarbonyl]-cyclohexylmethyl}-N-hydroxy-formamide
N-{4,4-Dimethyl-1-[N'-(4-trifluoromethyl-6-morpholin-4-yl-pyrimidin-2-yl)-hydrazinocarbonyl]-cyclohexylmethyl}-N-hydroxy-formamide
N-{4,4-Dimethyl-1-[N'-(7-methyl-benzo[1,2,4]triazin-3-yl)-hydrazinocarbonyl]-cyclohexylmethyl}-N-hydroxy-formamide
N-{4,4-Dimethyl-1-[N'-(5-methyl-benzo[1,2,4]triazin-3-yl)-hydrazinocarbonyl]-cyclohexylmethyl}-N-hydroxy-formamide
N-{4,4-Dimethyl-1-[N'-(4-methyl-pyridin-2-yl)-hydrazinocarbonyl]-cyclohexylmethyl}-N-hydroxy-formamide
N-{1-[N'-(Dimethylamino-ethyl-[1,3,5]triazin-2-yl)-hydrazinocarbonyl]-4,4-dimethyl-cyclohexylmethyl}-N-hydroxy-formamide
Benzofuran-2-carboxylic acid {[(1-{-[(formyl-hydroxy-amino)-methyl]-4,4-dimethyl-cyclohexyl}-methanoyl)-amino]-methyl}-amide
N-Hydroxy-N-{1-[N'-(4-trifluoromethyl-pyrimidin-2-yl)-hydrazinocarbonyl]-cycloheptylmethyl}-formamide
N-Hydroxy-N-{1-[N'-(4-methyl-pyrimidin-2-yl)-hydrazinocarbonyl]-cycloheptylmethyl}-formamide
N-Hydroxy-N-{1-[N'-(4-methyl-6-morpholin-4-yl-pyrimidin-2-yl)-hydrazinocarbonyl]-cycloheptylmethyl}-formamide
N-(1-{N'-[4-(4-Ethyl-piperazin-1-yl)-6-methyl-pyrimidin-2-yl]-hydrazinocarbonyl}-cycloheptylmethyl)-N-hydroxy-formamide
N-Hydroxy-N-{1-[N'-(4-methyl-pyridin-2-yl)-hydrazinocarbonyl]-cycloheptylmethyl}-formamide
N-Hydroxy-N-{1-[N'-(5-methyl-benzo[1,2,4]triazin-3-yl)-hydrazinocarbonyl]-cycloheptylmethyl}-formamide
N-Hydroxy-N-{1-[N'-(7-methyl-benzo[1,2,4]triazin-3-yl)-hydrazinocarbonyl]-cycloheptylmethyl}-formamide
N-Hydroxy-N-{1-[N'-(7-methoxy-benzofuran-2-carbonyl)-hydrazinocarbonyl]-cycloheptylmethyl}-formamide; and
Benzofuran-2-carboxylic acid {[(1-{-[(formyl-hydroxy-amino)-methyl]-cycloheptyl}-methanoyl)-amino]-methyl}-amide More preferred compounds in the present invention are selected from the group consisting of:
N-Hydroxy-N-{cis-4-methyl-1-[N'-(4-trifluoromethyl-pyrimidin-2-yl)-hydrazinocarbonyl]-cyclohexylmethyl}-formamide
N-Hydroxy-N-{cis-4-methyl-1-[N'-(4-methyl-pyrimidin-2-yl)-hydrazinocarbonyl]-cyclohexylmethyl}-formamide
N-Hydroxy-N-{cis-4-methyl-1-[N'-(4-morpholin-4-yl-6-trifluoromethyl-pyrimidin-2-yl)-hydrazinocabonyl]-cyclohexylmethyl}-formamide
N-Hydroxy-N-{cis-4-methyl-1-[N'-(7-methyl-benzo[1,2,4]triazin-3-yl)-hydrazinocarbonyl]-cyclohexylmethyl}-formamide
N-Hydroxy-N-{cis-4-methyl-1-[N'-(5-methyl-benzo[1,2,4]triazin-3-yl)-hydrazinocarbonyl]-cyclohexylmethyl}-formamide
N-Hydroxy-N-{cis-4-methyl-1-[N'-(5,7-dimethyl-benzo[1,2,4]triazin-3-yl)-hydrazinocarbonyl]-cyclohexylmethyl}-formamide
Benzofuran-2-carboxylic acid {[(cis-1-{1-[(formyl-hydroxy-amino)-methyl]-4-methyl-cyclohexyl}-methanoyl)-amino]-methyl}-amide
N-Hydroxy-N-(cis-1-{N'-[1-(7-methoxy-benzofuran-2-yl)-methanoyl]-hydrazinocarbonyl}-4-methyl-cyclohexylmethyl)-formamide General Synthetic Sequence The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1) that can be prepared from the common racemic intermediate (8), or common chiral intermediates (17) and (25).

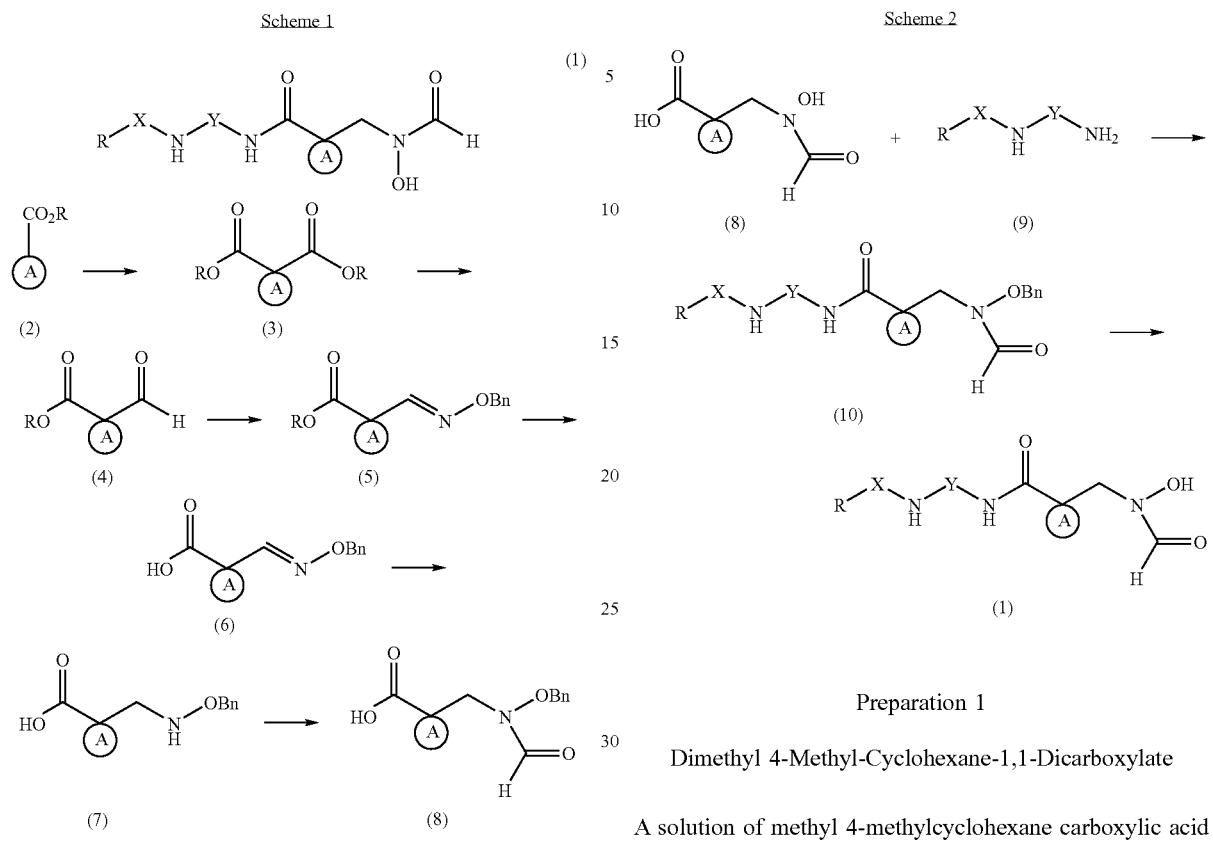

wherein:
A represents an optionally sustituted carbocycle of 3 to 8 membered ring;
R represents alkyl.

As shown in Scheme 1, intermediate (8) can be prepared by reacting the carbocyclic ester (2) with a base, such as lithium diisopropylamine, in an appropriate solvent, such as tetrahydrofuran, to afford the di-ester (3). Reduction (3) with diisobutyl aluminumhydride, in an appropriate solvent, such as dichloromethane or diethyl ether, at −78° C. gives the aldehyde (4). Reaction of the aldehyde functionality of compound (4) with O-benzylhydroxylamine in the presence of sodium acetate, provides the oxime (5). Hydrolysis of the ester functionality of compound (5) with a base, such as lithium hydroxide in an appropriate solvent mixture, such as THF—H$_2$O, at elevated temperatures gives acid (6). Reduction of the oxime of compound (6) using an appropriate reducing agent, such as sodium cyanoborohydride under acidic conditions in an appropriate solvent, such as methanol, yields the hydroxylamine (7). Formylation of the amine group of (7) is achieved using formic acid and acetic anhydride in a solvent, such as dichloromethane, to provide the formylated compound (8).

As shown in Scheme 2, coupling of (8) with hydrazines (9), using conditions such as DMAP/EDCI or EDCI/HOAt/NMM, provides (10), which can be debenzylated by hydrogenation using a catalyst, such as 10% Pd/C, in an appropriate solvent, such as methanol, to give the desired compound (1).

Preparation 1

Dimethyl 4-Methyl-Cyclohexane-1,1-Dicarboxylate

A solution of methyl 4-methylcyclohexane carboxylic acid (6.5 g, 41.6 mmol) in THF (15 mL) was added dropwise to a solution of lithium diisopropylamine (6.75 g, 62.4 mmol) in THF (60 mL) at −78° C. After stirring for 1 h at the same temperature, a solution of methylchloroformate (5.9 g, 62.4 mmol) in THF (15 mL) was added slowly and the mixture was allowed to warm to room temperature. After 18 h the reaction mixture was quenched with saturated aqueous NH$_4$Cl solution (100 mL). THF was removed in vacuo and the aqueous residue was extracted with dichloromethane (100 mL×3). The combined organic layers were dried (MgSO$_4$). After removal of the solvent under reduced pressure, purification by flash column chromatography using an eluting system of hexane/EtOAc (95:5) yielded the title compound as a clear colorless liquid (4.79 g, 54%). MH+215.

Preparation 2 cis-1-Formyl-4-methyl-cyclohexanecarboxylic acid methyl ester

To a solution of dimethyl 4-methyl-cyclohexane-1,1-dicarboxylate (4.79 g, 22.36 mmol) in dichloromethane (50 mL) at −78° C. under an nitrogen atmosphere was added diisobutylaluminum hydride (1.5M in toluene, 30 mL, 44.72 mmol) dropwise. After 4 h, the reaction mixture was quenched with saturated aqueous NH$_4$Cl solution (50 mL), then 1N HCl (50 mL) and allowed to warm to room temperature. The mixture was filtered through Celite@ and the organic phase was separated, was dried (MgSO4) and was evaporated in vacuo to yield the title compound which was used without further purification. MH+185.

Preparation 3

Cis-1-(Benzyloxyimino-Methyl)-4-Methyl-CyclohexaneCarboxylic Acid Methyl Ester A mixture of crude cis-1-formyl-4-methyl-cyclohexanecarboxylic acid methyl ester from Preparation 2 (22.4 mmol theoretical), sodium acetate (3.1 g, 44.72 mmol) and O-benzylhydroxylamine hydrochloride (7.1 g, 44.72 mmol) were stirred in methanol (120 mL) for 48 h. The methanol was removed in vacuo and the residue was purified by flash column chromatography using an eluting system of hexane/EtOAc (99:1 to 95:5) to yield the title compound as a clear colorless oil (2.1 g, 32%). MH+290.

Preparation 4

Cis-1-(Benzyloxyimino-Methyl)-4-Methyl-CyclohexaneCarboxylic Acid

A mixture of cis-1-(benzyloxyimino-methyl)-4-methyl-cyclohexanecarboxylic acid methyl ester (1.9 g, 6.57 mmol) and lithium hydroxide monohydrate (2.75 g, 65.7 mmol) in THF (20 mL) and water (7 mL) was heated at 65° C. for 18 h. The reaction mixture was acidified to pH 4 with 3N aqueous HCl and was extracted with ethyl acetate (50 mL×3). The combined organic layers were dried (MgSO$_4$) and were evaporated in vacuo to yield the title compound as a pale yellow oil. (1.8 g, 100%). MH+276.

Preparation 5

Cis-1-(Benzyloxyamino-Methyl)-4-Methyl-CyclohexaneCarboxylic Acid

To a solution of cis-1-(benzyloxyimino-methyl)-4-methyl-cyclohexanecarboxylic acid (1.8 g, 6.54 mmol) in methanol (60 mL) at 0° C. under a nitrogen atmosphere was added a trace amount of methyl orange. A solution of saturated methanolic HCl was added until a persistent red color was observed. Sodium cyanoborohydride (0.49 g, 7.85 mmol) was added portionwise alternately with methanolic HCl to maintain the red color. The reaction mixture was maintained at 0° C. for an additional 2 h and the volatiles were removed in vacuo. The product was used without further purification. MH+278.

Preparation 6

Cis-1-[(Benzyloxy-Formyl-Amino)-Methyl]-4-Methyl-Cyclohexanecarboxylic Acid

To a cold solution of formic acid (15 mL, 0.39 mol) in dichloromethane (30 mL) at 0° C. under a nitrogen atmosphere was added acetic anhydride (6.2 mL, 65.4 mmol). After 1 h, solution of cis-1-(benzyloxyamino-methyl)-4-methyl-cyclohexanecarboxylic acid from Preparation 5 (6.54 mmol theoretical) in dichloromethane (20 mL) was added. The mixture was maintained at 0° C. for 2.5 h and was concentrated in vacuo. Water (100 mL) was added and the mixture was extracted with dichloromethane (100 mL×2). The combined organic extracts were dried (MgSO$_4$) and were evaporated in vacuo. The residue was purified by preparative HPLC to yield the title compound as a white solid (0.88 g, 44%). MH+306.

Preparation 7

N-Benzyloxy-N-{Cis-4-Methyl-1-[N'-(4-TrifluoroMethyl-Pyrimidin-2-yl)-Hydrazinocarbonyl]-CycloHexylmethyl}-Formamide To a mixture of cis-1-[(benzyloxy-formyl-amino)-methyl]-4-methyl-cyclohexanecarboxylic acid (0.075 g, 0.25 mmol), 2-hydrazino-4-(trifluoromethyl)pyrimidine (0.068 g, 0.29 mmol), NMM (0.075 g, 0.75 mmol) and HOAt (0.04 g, 0.29 mmol) in DMF (1 mL) at room temperature was added 1-[3-(dimethylamino)-propyl]-3-ethylcarbodiimide hydrochloride (0.057 g, 0.29 mmol). After stirring at room temperature 18 h, the reaction mixture was then purified by HPLC to afford the title compound as a white solid (0.08 g, 70%). MH+466.

Preparation 8

Dimethyl Cyclopentane-1,1-Dicarboxylate

A solution of methyl cyclopentanecarboxylic acid (7.1 g, 38.16 mmol) in THF (14 mL) was added dropwise to a solution of lithium diisopropylamine (6.62 g, 61.2 mmol) in THF (55 mL) at −78° C. After stirring for 1 h at the same temperature, a solution of methylchloroformate (5.78 g, 61.2 mmol) in THF (14 mL) was added slowly and the mixture was allowed to warm to room temperature. After 18 h the reaction mixture was quenched with saturated aqueous NH$_4$Cl solution (100 mL). THF was removed in vacuo and the aqueous residue was extracted with dichloromethane (100 mL×3). The combined organic layers were dried (MgSO$_4$). After removal of the solvent under reduced pressure, purification by flash column chromatography using an eluting system of hexane/EtOAc (95:5) yielded the title compound as a clear colorless liquid (7.1 g, 93%). MH+187.

Preparation 9

1-Formyl-Cyclopentanecarboxylic Acid Methyl Ester

To a solution of dimethyl cyclopentane-1,1-dicarboxylate (7.1 g, 38.1 mmol) in dichloromethane(75 mL) at −78° C. under an nitrogen atmosphere was added diisobutylaluminum hydride (1.5M in toluene, 51 mL, 76 mmol) dropwise. After 4 h, the reaction mixture was quenched with saturated aqueous NH$_4$Cl solution (30 mL), then 1N HCl (38 mL) and allowed to warm to room temperature. The mixture was filtered through Celite@ and the organic phase was separated, was dried (MgSO4) and was evaporated in vacuo to yield the title compound which was used without further purification (3.1 g, 52%). MH+157.

Preparation 10

1-(Benzyloxyimino-Methyl)-Cyclopentanecarboxylic Acid Methyl Ester

A mixture of 1-formyl-cyclopentanecarboxylic acid methyl ester (3.1 g, 19.8 mmol), sodium acetate (2.74 g, 39.72 mmol) and O-benzylhydroxylamine hydrochloride (6.34 g, 39.7 mmol) were stirred in methanol (120 mL) for 18 h. The methanol was removed in vacuo and the residue partitioned between water and EtOAc. The aqueous phase was extracted with EtOAc (50 mL×2). The combined organic extracts were dried (MgSO4) and were evaporated in vacuo. Purification by flash column chromatography using an eluting system of hexane/EtOAc (95:5 to 90:10) provided the title compound as a clear colorless oil (2.26 g, 44%). MH+262.

Preparation 11

1-(Benzyloxyimino-Methyl)-Cyclopentanecarboxylic Acid

A mixture of 1-(benzyloxyimino-methyl)-cyclopentanecarboxylic acid methyl ester (2.26 g, 8.65 mmol) and sodium hydroxide (1.0 g, 25.9 mmol) in THF (15 mL), methanol (15 mL) and water (5 mL) was stirred at room temperature for 18 h. The reaction mixture was acidified to pH 4 with 3N aqueous HCl and was extracted with dichloromethane (50 mL×3). The combined organic layers were dried (MgSO$_4$) and were evaporated in vacuo to yield the title compound as a pale yellow oil. (1.91 g, 89%). MH+248.

Preparation 12

1-(Benzyloxyamino-Methyl)-Cyclopentanecarboxylic Acid

To a solution of 1-(benzyloxyimino-methyl)-cyclopentanecarboxylic acid (1.91 g, 7.72 mmol) in methanol (70 mL) at 0° C. under a nitrogen atmosphere was added a trace amount of methyl orange. A solution of saturated methanolic HCl was added until a persistent red color was observed. Sodium cyanoborohydride (0.58 g, 9.27 mmol) was added portionwise alternately with methanolic HCl to maintain the red color. The reaction mixture was maintained at 0° C. for an additional 3 h and the volatiles were removed in vacuo. The residue was purified by preparative reverse-phase HPLC to yield the title compound as a pale, yellow oil (1.1 g, 57%). MH+250.

Preparation 13

1-[(Benzyloxy-Formyl-Amino)-Methyl]-Cyclopentanecarboxylic Acid

To a cold solution of formic acid (10.3 mL, 0.27 mol) in dichloromethane (40 mL) at 0° C. under a nitrogen atmosphere was added acetic anhydride (4.2 mL, 44.1 mmol). After 1 h, a solution of 1-(benzyloxyamino-methyl)-cyclopentanecarboxylic acid (1.1 g, 4.41 mmol) in dichloromethane (20 mL) was added. The mixture was stirred at room temperature for 18 h and was concentrated in vacuo. Water (100 mL) was added and the mixture was extracted with dichloromethane (100 mL×2). The combined organic extracts were dried (MgSO$_4$) and were evaporated in vacuo to yield the title compound as a pale, yellow oil (1.05 g, 86%). MH+278.

Preparation 14

N-Benzyloxy-N-{1-[N'-(4-Trifluoromethyl-Pyrimidin-2-Yl)-Hydrazinocarbonyl]-Cyclopentylmethyl}-Formamide To a mixture of 1-[(Benzyloxy-formyl-amino)-methyl]-cyclopentanecarboxylic acid (0.10 g, 0.36 mmol), 2-hydrazino-4-(trifluoromethyl)pyrimidine (0.10 g, 0.43 mmol), NMM (0.11 g, 1.08 mmol) and HOAt (0.059 g, 0.43 mmol) in DMF (2 mL) at room temperature was added 1-[3-(dimethylamino)-propyl]-3-ethylcarbodiimide hydrochloride (0.085 g, 0.43 mmol). After stirring at room temperature 18 h, the reaction mixture was then purified by preparative, reverse-phase HPLC to afford the title compound as a white solid (0.085 g, 57%). MH+438.

Preparation 15

Dimethyl Cyclohexane-1,1-Dicarboxylate

A solution of methyl cyclohexanecarboxylic acid (2.0 g, 14.06 mmol) in THF (5 mL) was added dropwise to a solution of lithium diisopropylamine (2.28 g, 21.1 mmol) in THF (20 mL) at −78° C. After stirring for 1 h at the same temperature, a solution of methylchloroformate (2.0 g, 21.1 mmol) in THF (5 mL) was added slowly and the mixture was allowed to warm to room temperature. After 18 h the reaction mixture was quenched with saturated aqueous NH$_4$Cl solution (20 mL). THF was removed in vacuo and the aqueous residue was extracted with EtOAc (50 mL×3). The combined organic layers were dried (MgSO$_4$). After removal of the solvent under reduced pressure, purification by flash column chromatography using an eluting system of hexane/EtOAc (80:20) yielded the title compound (2.8 g, 99%). MH+201.

Preparation 16

1-Formyl-Cyclohexanecarboxylic Acid Methyl Ester

To a solution of dimethyl cyclohexane-1,1-dicarboxylate (2.8 g, 14.0 mmol) in dichloromethane(55 mL) at −78° C. under a nitrogen atmosphere was added diisobutylaluminum hydride (1.5M in toluene, 19 mL, 28 mmol) dropwise. After 3 h, the reaction mixture was quenched with saturated aqueous NH$_4$Cl solution (11 mL), then 1N HCl (14 mL) and allowed to warm to room temperature. The mixture was filtered through Celite@ and the organic phase was separated, was dried (MgSO4) and was evaporated in vacuo to yield the title compound which was used without further purification (1.23 g, 52%). MH+171.

Preparation 17

1-(Benzyloxyimino-Methyl)-Cyclohexanecarboxylic Acid Methyl Ester

A mixture of 1-formyl-cyclohexanecarboxylic acid methyl ester (1.23 g, 7.23 mmol), sodium acetate (1.0 g, 14.5 mmol) and O-benzylhydroxylamine hydrochloride (2.3 g, 14.5 mmol) were stirred in methanol (40 mL) for 18 h. The methanol was removed in vacuo and the residue partitioned between water and EtOAc. The aqueous phase was extracted with EtOAc (50 mL×2). The combined organic extracts were dried (MgSO4) and were evaporated in vacuo to provide the title compound as a clear colorless liquid (1.75 g, 88%). MH+276.

Preparation 18

1-(Benzyloxyimino-Methyl)-Cyclohexanecarboxylic Acid

A mixture of 1-(benzyloxyimino-methyl)-cyclohexanecarboxylic acid methyl ester (1.75 g, 6.36 mmol) and sodium hydroxide (0.76 g, 19.1 mmol) in THF (10 mL), methanol (10 mL) and water (5 mL) was stirred at room temperature for 40 h. The reaction mixture was acidified to pH 4 with 3N aqueous HCl and was extracted with EtOAc (50 mL×2). The combined organic layers were dried (MgSO4) and were evaporated in vacuo to yield the title compound as a yellow oil. (1.59 g, 96%). MH+262.

Preparation 19

1-(Benzyloxyamino-Methyl)-Cyclohexanecarboxylic Acid

To a solution of 1-(benzyloxyimino-methyl)-cyclohexanecarboxylic acid (1.59 g, 6.08 mmol) in methanol (40 mL) at 0° C. under a nitrogen atmosphere was added a trace amount of methyl orange. A solution of saturated methanolic HCl was added until a persisten red color was observed. Sodium cyanoborohydride (0.42 g, 6.69 mmol) was added portionwise alternately with methanolic HCl to maintain the red color. The reaction mixture was maintained at 0° C. for an additional 3 h and the volatiles were removed in vacuo to yield the title compounds as a pale, yellow oil that was used without further purification. MH+264.

Preparation 20

1-[(Benzyloxy-Formyl-Amino)-Methyl]-Cyclohexanecarboxylic Acid

To a cold solution of formic acid (15.3 mL, 0.4 mol) in dichloromethane (100 mL) at 0° C. under a nitrogen atmosphere was added acetic anhydride (5.75 mL, 60 mmol). After 1 h, a solution of 1-(benzyloxyamino-methyl)-cyclohexanecarboxylic acid from Preparation 19 (4.41 mmol theoretical) in dichloromethane (50 mL) was added. The mixture was stirred at room temperature for 18 h and was concentrated in vacuo. Brine (100 mL) was added and the mixture was extracted with dichloromethane (100 mL×2). The combined organic extracts were dried (MgSO$_4$) and were evaporated in vacuo to yield the title compound as a pale, orange oil (1.77 g, 100%). MH+292.

Preparation 21

N-Benzyloxy-N-{1-[N'-(4-Trifluoromethyl-Pyrimidin-2-yl)-Hydrazinocarbonyl]-Cyclohexylmethyl}-Formamide To a mixture of 1-[(Benzyloxy-formyl-amino)-methyl]-cyclohexanecarboxylic acid (0.10 g, 0.34 mmol), 2-hydrazino-4-(trifluoromethyl)pyrimidine (0.06 g, 0.34 mmol), NMM (0.17 g, 1.7 mmol) and HOAt (0.046 g, 0.34 mmol) in DMF (2 mL) at room temperature was added 1-[3-(dimethylamino)-propyl]-3-ethylcarbodiimide hydrochloride (0.067 g, 0.34 mmol). After stirring at room temperature 18 h, the reaction mixture was then purified by preparative, reverse-phase HPLC to afford the title compound as a white solid (0.070 g, 47%). MH+452.

Preparation 22

4,4-Dimethyl Cyclohexanone

To a solution of 4,4-dimethyl-cyclohex-2-enone (17.8 g, 0.14 mol) in EtOAC (290 mL) was added 10% Pd/C (0.36 g). The reaction mixture was subjected to hydrogenation for 8 h at room temperature. The reaction mixture was then filtered through a pad of Celite@, and washed with EtOAc (500 mL). Removal of the solvent provided the title compound as a white wax (15.6 g, 86%). MH+127.

Preparation 23

2-(4,4-Dimethyl-Cyclohexylidene)-[1,3]Dithiane

To a solution of 2-trimethylsily-1,3-dithiane (42.3 g, 0.22 mol) in THF (400 mL) at 0° C. under an argon atmosphere was added a solution of n-butyl lithium (2.5 M in hexanes, 88 mL, 0.22 mol) and the mixture was cooled to −78° C. A solution of 4,4-dimethyl cyclohexanone (13.9 g, 0.11 mol) in THF (50 mL) was added over 10 min. After 2 h the reaction mixture was quenched with saturated aqueous NH$_4$Cl solution (200 mL). The aqueous phase was extracted with EtOAc (200 mL×2) and the combined organic layers were dried (MgSO$_4$) and were evaporated. The reaction by-products were removed by vacuum distillation to yield the desired product as a white wax (21 g, 85%). MH+229

Preparation 24

4,4-Dimethyl-Cyclohexanecarboxylic Acid 2-(4,4-Dimethyl-cyclohexylidene)-[1,3]dithiane (21.6 g, 95 mmol) and TFA (30.5 mL, 0.32 mol) were placed in acetonitrile (100 mL) and water (25 mL) and the mixture was heated at 65° C. for 3 h. 30% Aqueous hydrogen peroxide (152 mL, 1.3 mol) was added carefully and the mixture was warmed to 80° C. slowly. After 1 h, the reaction mixture was cooled to 40° C. and was added slowly to an aqueous solution of NaOH (6N, 630 mL). The resulting mixture was cooled to 0° C. and acidified with aqueous 6N HCl. Dichloromethane (500 mL) was added and the mixture was filtered. The aqueous phase was extracted with dichloromethane (100 mL×5), was dried (MgSO4) and was evaporated in vacuo to yield the title compound (12 g, 81%). MH+157.

Preparation 25

Methyl 4,4-Dimethyl-Cyclohexanearboxylate 4,4-Dimethyl cyclohexanecarboxylic acid (11.97 g, 77 mmol) was heated at 45° C. in saturated methanolic HCl (300 mL) for 4 h. The volatiles were removed in vacuo and the residue was purified by flash column chromatography using an eluting system of hexane/EtOAc (95:5) to provide the title compound as a pale orange oil (7.17 g, 55%). MH+171.

Preparation 26

Dimethyl 4,4-Dimethylcyclohexane-1,1-Dicarboxylate

A solution of methyl 4,4-dimethyl-cyclohexane carboxylic acid (7.17 g, 42.2 mmol) in THF (15 mL) was added dropwise to a solution of lithium diisopropylamine (6.84 g, 63.3 mmol) in THF (60 mL) at −78° C. After stirring for 1 h at the same temperature, a solution of methylchloroformate (6.0 g, 63.3 nmol) in THF (15 mL) was added slowly and the mixture was allowed to warm to room temperature. After 18 h the reaction mixture was quenched with saturated aqueous NH$_4$Cl solution (150 mL) and the aqueous residue was extracted with EtOAc (100 mL×5). The combined organic layers were dried (MgSO$_4$). After removal of the solvent under reduced pressure, purification by flash column chromatography using an eluting system of hexane/EtOAc (95:5) yielded the title compound as a clear colorless liquid (5.23 g, 54%). MH+229.

Preparation 27

1-Formyl-4,4-Dimethyl-Cyclohexanecarboxylic Acid Methyl Ester

To a solution of dimethyl 4,4-dimethyl-cyclohexane-1,1-dicarboxylate (5.23 g, 22.9 mmol) in diethyl ether (250 mL) at −78° C. under a nitrogen atmosphere was added diisobutylaluminum hydride (1.5M in toluene, 30.6 mL, 45.9 mmol) dropwise. After 2.5 h, the reaction mixture was quenched with a mixture of methanol (75 mL) and water (75 mL). The mixture was filtered through Celite@ and the aqueous phase was extracted with diethyl ether (100 mL×5), was dried (MgSO4) and was evaporated in vacuo to yield the title compound which was used without further purification. MH+199.

Preparation 28

1-(Benzyloxyimino-Methyl)-4,4-Dimethyl-Cyclohexanecarboxylic Acid Methyl Ester A mixture of crude 1-formyl-4,4-dimethyl-cyclohexanecarboxylic acid methyl ester from Preparation 27 (22.9 mmol theoretical), sodium acetate (3.76 g, 45.8 mmol) and O-benzylhydroxylamine hydrochloride (7.32 g, 45.8 mmol) were stirred in methanol (100 mL) for 18 h. The methanol was removed in vacuo, water (100 mL) was added and the aqueous phase was extracted with EtOAc (50 mL×5). The combined organic extracts were dried (MgSO$_4$) and were evaporated in vacuo. The residue was purified by flash column chromatography using an eluting system of hexane/EtOAc (99:1) to yield the title compound (1.83 g, 26%). MH+304.

Preparation 29

1-(Benzyloxyimino-Methyl)-4,4-Dimethyl-Cyclohexanecarboxylic Acid

A mixture of 1-(benzyloxyimino-methyl)-4,4-dimethyl-cyclohexanecarboxylic acid methyl ester (1.83 g, 6.04 mmol) and lithium hydroxide monohydrate (2.53 g, 60.4 mmol) in THF (60 mL) and water (30 mL) was heated at 60° C. for 18 h. The reaction mixture was acidified to pH 5 with 3N aqueous HCl and was extracted with dichloromethane (50 mL×6). The combined organic layers were dried (MgSO$_4$) and were evaporated in vacuo to yield the title compound as a pale yellow oil. (1.47 g, 84%). MH+290.

Preparation 30

1-(Benzyloxyamino-Methyl)-4,4-Dimethyl-Cyclohexanecarboxylic Acid

A solution of 1-(benzyloxyimino-methyl)-4,4-dimethyl-cyclohexanecarboxylic acid (1.47 g, 5.11 mmol) in methanol (100 mL) at 0° C. under a nitrogen atmosphere was added a trace amount of methyl orange. A solution of saturated methanolic HCl was added until a persistent red color was observed. Sodium cyanoborohydride (0.42 g, 6.68 mmol) was added portionwise alternately with methanolic HCl to maintain the red color. The reaction mixture was maintained at 0° C. for an additional 2 h and the volatiles were removed in vacuo. The product was used without further purification. MH+292.

Preparation 31

1-[(Benzyloxy-Formyl-Amino)-Methyl]-4,4-Dimethyl-Cyclohexanecarboxylic Acid

To a cold solution of formic acid (12.8 mL, 0.33 mol) in dichloromethane (50 mL) at 0° C. under a nitrogen atmosphere was added acetic anhydride (4.8 mL, 51 mmol). After 1 h, a solution of 1-(benzyloxyamino-methyl)-4,4-dimethyl-cyclohexanecarboxylic acid from Preparation 30 (5.11 mmol theoretical) in dichloromethane (50 mL) was added. The reaction was stirred at room temperature for 18 h and was concentrated in vacuo. Water (100 mL) was added and the mixture was extracted with dichloromethane (50 mL×5). The combined organic extracts were dried (MgSO$_4$) and were evaporated in vacuo to yield the title compound (1.55 g, 95%). MH+320.

Preparation 32

N-Benzyloxy-N-{4,4-Dimethyl-1-[N'-(4-Trifluoromethyl-Pyrimidin-2-yl)-hydrazinocarbonyl]-Cyclohexylmethyl}-Form Amide To a mixture of 1-[(benzyloxy-formyl-amino)-methyl]-4,4-dimethyl-cyclohexanecarboxylic acid (0.10 g, 0.31 mmol), 2-hydrazino-4-(trifluoromethyl)pyrimidine (0.067 g, 0.37 mmol), NMM (0.095 g, 0.93 mmol) and HOAt (0.05 g, 0.37 mmol) in DMF (1 mL) at room temperature was added 1-[3-(dimethylamino)-propyl]-3-ethylcarbodiimide hydrochloride (0.072 g, 0.37 mmol). After stirring at room temperature 18 h, the reaction mixture was then purified by preparative, reverse-phase HPLC to afford the title compound as a white solid (0.11 g, 74%). MH+480.

Preparation 33

Dimethyl Cycloheptane-1,1-Dicarboxylate

A solution of methyl cycloheptanecarboxylic acid (8.0 g, 51.2 mmol) in THF (18 mL) was added dropwise to a solution of lithium diisopropylamine (8.3 g, 76.8 mmol) in THF (70 mL) at −78° C. After stirring for 1 h at the same temperature, a solution of methylchloroformate (7.26 g, 76.8 mmol) was added slowly and the mixture was allowed to warm to room temperature. After 18 h the reaction mixture was quenched with saturated aqueous NH$_4$Cl solution (100 mL) and was extracted with EtOAc (100 mL×3). The combined organic layers were dried (MgSO$_4$). After removal of the solvent under reduced pressure, purification by flash column chromatography using an eluting system of hexane/EtOAc (95:5) yielded the title compound as a clear, colorless liquid (7.8 g, 71%). MH+215.

Preparation 34

1-Formyl-Cyclohexanecarboxylic Acid Methyl Ester

To a solution of dimethyl cycloheptane-1,1-dicarboxylate (7.62 g, 35.6 mmol) in diethyl ether (250 mL) at −78° C. under an argon atmosphere was added diisobutylaluminum hydride (1.5M in toluene, 48 mL, 72 mmol) dropwise. After 1.5 h, the reaction mixture was quenched with a mixutre of methanol (100 mL) and water (100 mL), was filtered through Celite@ and was extracted with diethyl ether (100 mL×3). The combined organic extracts were dried (MgSO4), were filtered and were evaporated in vacuo to yield the title compound which was used without further purification. MH+185.

Preparation 35

1-(Benzyloxyimino-Methyl)-Cycloheptanecarboxylic Acid Methyl Ester

A mixture of 1-formyl-cycloheptanecarboxylic acid methyl ester from Preparation 34 (35.6 mmol theoretical), sodium acetate (5.84 g, 72 mmol) and O-benzylhydroxylamine hydrochloride (11.36 g, 72 mmol) were stirred in methanol (71 mL) for 2 h. The methanol was removed in vacuo and the residue partitioned between water and EtOAc. The aqueous phase was extracted with EtOAc (50 mL×5). The combined organic extracts were dried (MgSO4) and were evaporated in vacuo. Purifiaction by flash column chromatography using an eluting sytem of hexanes/EtOAc (99:1) provided the title compound as a clear colorless oil (5.22 g, 51%). MH+290.

Preparation 36

1-(Benzyloxyimino-Methyl)-Cycloheptanecarboxylic Acid

A mixture of 1-(benzyloxyimino-methyl)-cycloheptanecarboxylic acid methyl ester (5.2 g, 18 mmol) and lithium hydroxide monohydrate (7.56 g, 180 mmol) in THF (80 mL) and water (40 mL) was stirred at 60° C., for 24 h. The THF was removed in vacuo and the reaction mixture was acidified to pH 4 with 6N aqueous HCl and was extracted with dichloromethane (50 μL×5). The combined organic layers were dried (MgSO$_4$) and were evaporated in vacuo to yield the title compound (4.44 g, 90%). MH+276.

Preparation 37

1-(Benzyloxyamino-Methyl)-Cycloheptanecarboxylic Acid

A solution of 1-(benzyloxyimino-methyl)-cycloheptanecarboxylic acid (4.44 g, 16.1 mmol) in methanol (200 mL) at 0° C. under an argon atmosphere was added a trace amount of methyl orange. A solution of saturated methanolic HCl was added until a persistent red color was observed. Sodium cyanoborohydride (1.3 g, 20.9 mmol) was added portionwise alternately with methanolic HCl to maintain the red color. The reaction mixture was maintained at 0° C. for an additional 2 h and the volatiles were removed in vacuo to yield the title compound that was used without further purification. MH+278.

Preparation 38

1-[(Benzyloxy-Formyl-Amino)-Methyl]-Cycloheptanecarboxylic Acid

To a cold solution of formic acid (40.2 mL, 1.04 mol) in dichloromethane (150 mL) at 0° C. under a nitrogen atmosphere was added acetic anhydride (15.2 mL, 160 mmol). After 1 h, a solution of 1-(benzyloxyamino-methyl)-cycloheptanecarboxylic acid from Preparation 37 (16.1 mmol theoretical) in dichloromethane (150 mL) was added. The reaction was stirred at 0° C. for 3 h and was concentrated in vacuo. Water (150 mL) was added and the mixture was extracted with dichloromethane (50 mL×5). The combined organic extracts were dried (MgSO$_4$) and were evaporated in vacuo. Purification by preparative, reverse-phase HPLC provided the title compound (2.56 g, 52%). MH+306.

Preparation 39

N-Benzyloxy-N-{1-[N'-(4-Trifluoromethyl-Pyrimidin-2-yl)-Hydrazinocarbonyl]-Cycloheptylmethyl}-Formamide To a mixture of 1-[(Benzyloxy-formyl-amino)-methyl]-cycloheptanecarboxylic acid (0.10 g, 0.33 mmol), 2-hydrazino-4-(trifluoromethyl)pyrimidine (0.07 g, 0.39 mmol), NMM (0.10 g, 1.0 mmol) and HOAt (0.053 g, 0.39 mmol) in DMF (1 mL) at room temperature was added 1-[3-(dimethylamino)-propyl]-3-ethylcarbodiimide hydrochloride (0.075 g, 0.34 mmol). After stirring at room temperature 18 h, the reaction mixture was then purified by preparative, reverse-phase HPLC to afford the title compound as a white solid (0.11 g, 72%). MH+466.

Preparation 40

2-((3S,5R)-3,5-Dimethyl-Cyclohexylidene)-[1,3] Dithiane

To a solution of 2-trimethylsilyl-1,3-dithiane (30.1 g, 0.16 mol) in THF (250 mL) at 0° C. under an argon atmosphere was added a solution of n-butyl lithium (2.5 M in hexanes, 64 mL, 0.16 mol) and the mixture was cooled to −78° C. A solution of cis-3,5-dimethyl cyclohexanone (10 g, 0.079 mol) in THF (30 mL) was added over 10 min. After 3.5 h the reaction mixture was quenched with saturated aqueous NH$_4$Cl solution (100 mL). The aqueous phase was extracted with EtOAc (100 mL×4) and the combined organic layers were dried (MgSO$_4$) and were evaporated. The reaction by-products were removed by vacuum distillation to yield the desired product (16.6 g, 92%). MH+229

Preparation 41

(3S,5R)-3,5-Dimethyl-Cyclohexanecarboxylic Acid 2-((3S,5R)-3,5-Dimethyl-cyclohexylidene)-[1,3]dithiane (8.36 g, 0.036 mmol) and TFA (9.5 mL, 0.12 mol) were placed in acetonitrile (480 mL) and water (120 mL) and the mixture was heated at 65° C. for 1 h. 30% Aqueous hydrogen peroxide (48 mL, 0.49 mol) was added carefully and the mixture was warmed to 80° C. slowly. After 1 h, the reaction mixture was cooled to 40° C. and was added slowly to an aqueous solution of NaOH (6N, 475 mL). The resulting mixture was cooled to 0° C. and acidified with aqueous 6N HCl. The acetonitrile was removed by rotary evaporation. The residue was extracted with dichloromethane (100 mL×5) was dried (MgSO4) and was evaporated in vacuo to yield the title compound as a white wax (4.1 g, 72%). MH+157.

Preparation 42

(3S,5R)-3,5-Dimethyl-Cyclohexanecarboxylic Acid Methyl Ester (3S,5R)-3,5-Dimethyl-cyclohexanecarboxylic acid (8.1 g, 52 mmol) was heated at 45° C. in saturated methanolic HCl (200 mL) for 4 h. The volatiles were removed in vacuo and the residue was purified by flash column chromatography using an eluting system of hexane/EtOAc (95:5) to provide the title compound as a light yellow oil (5.7 g, 65%). MH+171.

Preparation 43

(3R,5S)-3,5-Dimethyl-Cyclohexane-1,1-Dicarboxylate

A solution of (3S,5R)-3,5-dimethyl-cyclohexanecarboxylic acid methyl ester (5.7 g, 33.5 mmol) in THF (20 mL) was added dropwise to a solution of lithium diisopropylamine (5.36 g, 50 mmol) in THF (50 mL) at −78° C. After stirring for 1.5 h at the same temperature, methylchloroformate (4.9 g, 50 mmol) in THF (15 mL) was added slowly and the mixture was allowed to warm to room temperature. After 18 h the reaction mixture was quenched with saturated aqueous NH$_4$Cl solution (100 mL) and the aqueous residue was extracted with EtOAc (75 mL×5). The combined organic layers were dried (MgSO$_4$). After removal of the solvent under reduced pressure, purification by flash column chromatography using an eluting system of hexane/EtOAc (95:5) yielded the title compound as a pale yellow oil (7.38 g, 97%). MH+229.

Preparation 44

(3S,5R)-1-Formyl-3,5-Dimethyl-Cyclohexanecarboxylic Acid Methyl Ester

To a solution of (3R,5S)-3,5-dimethyl-cyclohexane-1,1-dicarboxylate (7.38 g, 32.4 mmol) in diethyl ether (250 mL) at −78° C. under a nitrogen atmosphere was added diisobutylaluminum hydride (1.5M in toluene, 43 mL, 64.8 mmol) dropwise. After 2.5 h, the reaction mixture was quenched with saturated aqueous NH$_4$Cl solution (100 mL) then with 1N HCl solution (100 mL). The aqueous phase was extracted with diethyl ether (100 mL×5), was dried (MgSO4) and was evaporated in vacuo to yield the title compound as a clear, colorless oil (5.5 g, 85%) which was used without further purification. MH+199.

Preparation 45

(3S,5R)-1-(Benzyloxyimino-Methyl)-3,5-Dimethyl-Cyclohexanecarboxylic Acid Methyl Ester A mixture of (3S,5R)-1-formyl-3,5-dimethyl-cyclohexanecarboxylic acid methyl ester (5.5 g, 27.8 mmol), sodium acetate (4.57 g, 55.6 mmol) and O-benzylhydroxylamine hydrochloride (8.88 g, 55.6 mmol) were stirred in methanol (100 mL) for 18 h. The methanol was removed in vacuo, water (100 mL) was added and the aqueous phase was extracted with EtOAc (50 mL×5). The combined organic extracts were dried (MgSO$_4$) and were evaporated in vacuo. The residue was purified by flash column chromatography using an eluting system of hexane/EtOAc (99:1) to yield the title compound as a clear yellow oil (4.8 g, 57%). MH+304.

Preparation 46

(3S,5R)-1-(Benzyloxyimino-Methyl)-3,5-Dimethyl-Cyclohexanecarboxylic Acid

A mixture of (3S,5R)-1-(benzyloxyimino-methyl)-3,5-dimethyl-cyclohexanecarboxylic acid methyl ester (4.8 g, 15.8 mmol) and lithium hydroxide monohydrate (6.6 g, 158 mmol) in THF (170 mL) and water (85 mL) was heated at 90° C. for 48 h. The reaction mixture was acidified to pH 3 with 6N aqueous HCl and was extracted with dichloromethane (75 mL×6). The combined organic layers were dried (MgSO$_4$) and were evaporated in vacuo to yield the title compound as a pale yellow oil. (1.8 g, 39%). MH+290.

Preparation 47

(3S,5R)-1-(Benzyloxyamino-Methyl)-3,5-Dimethyl-Cyclohexanecarboxylic Acid

A solution of (3S,5R)-1-(benzyloxyimino-methyl)-3,5-dimethyl-cyclohexanecarboxylic acid (1.8 g, 6.2 mmol) in methanol (120 mL) at 0° C. under a nitrogen atmosphere was added a trace amount of methyl orange. A solution of saturated methanolic HCl was added until a persistent red color was observed. Sodium cyanoborohydride (0.51 g, 8.1 mmol) was added portionwise alternately with methanolic HCl to maintain the red color. The reaction mixture was maintained at 0° C. for an additional 0.5 h and the volatiles were removed in vacuo. The product was used without further purification. MH+292.

Preparation 48

(3S,5R)-1-[(Benzyloxy-Formyl-Amino)-Methyl]-3,5-Dimethyl-Cyclohexanecarboxylic Acid To a cold solution of formic acid (15.5 mL, 0.40 mol) in dichloromethane (75 mL) at 0° C. under a nitrogen atmosphere was added acetic anhydride (5.9 mL, 62 mmol). After 1 h, a solution of (3S,5R)-1-(Benzyloxyamino-methyl)-3,5-dimethyl-cyclohexanecarboxylic acid (1.8 g, 6.2 mmol) in dichloromethane (75 mL) was added. The reaction was stirred at room temperature for 18 h and was concentrated in vacuo. Water (150 mL) was added and the mixture was extracted with dichloromethane (75 mL×5). The combined organic extracts were dried (MgSO$_4$) and were evaporated in vacuo to yield the title compound as a yellow solid (1.59 g, 80%). MH+320.

Preparation 49

N-Benzyloxy-N-{(3S,5R)-3,5-Dimethyl-[N'-(4-Trifluoromethyl-Pyrimidin-2-yl)-Hydrazinocarbonyl]-Cyclohexylmethyl}-Formamide To a mixture of (3S,5R)-1-[(Benzyloxy-formyl-amino)-methyl]-3,5-dimethyl-cyclohexanecarboxylic acid (0.10 g, 0.31 mmol), 2-hydrazino-4(trifluoromethyl)pyrimidine (0.067 g, 0.37 mmol), NMM (0.095 g, 0.93 mmol) and HOAt (0.05 g, 0.37 mmol) in DMF (1 mL) at room temperature was added 1-[3-(dimethylamino)-propyl]-3-ethylcarbodiimide hydrochloride (0.072 g, 0.37 mmol). After stirring at room temperature 18 h, the reaction mixture was then purified by preparative, reverse-phase HPLC to afford the title compound as a white solid (0.10 g, 71%). MH+480.

Preparation 51

3-Butyl-Cyclobutane-1,1-Dicarboxylic Acid Dimethyl Ester

A solution of 3-butyl-cyclobutanecarboxylic acid methyl ester (7.75 g, 45.6 mmol) in THF (30 mL) was added dropwise to a solution of lithium diisopropylamine (7.26 g, 68.4 mmol) in THF (70 mL) at −78° C. After stirring for 1.5 h at the same temperature, methyl chloroformate (6.46 g, 68.4 mmol) was added slowly and the mixture was allowed to warm to room temperature. After 18 h the reaction mixture was quenched with saturated aqueous NH$_4$Cl solution (200 mL) and the aqueous residue was extracted with EtOAc (75 mL×5). The combined organic layers were dried (MgSO$_4$). After removal of the solvent under reduced pressure, purification by flash column chromatography using an eluting system of hexane/EtOAc (95:5) yielded the title compound as a clear yellow oil (8.37 g, 81%). MH+229.

Preparation 52

3-Butyl-1-Formyl-Cyclobutanecarboxylic Acid Methyl Ester

To a solution of 3-butyl-cyclobutane-1,1-dicarboxylic acid dimethyl ester (8.37 g, 36.7 mmol) in diethyl ether (300 mL) at −78° C. under a nitrogen atmosphere was added diisobutylaluminum hydride (1.5M in toluene, 49 mL, 73.4 mmol) dropwise. After 2.5 h, the reaction mixture was quenched with saturated aqueous NH$_4$Cl solution (150 mL) then with 1N HCl solution (150 mL). The aqueous phase was extracted with diethyl ether (100 mL×5), was dried (MgSO4) and was evaporated in vacuo to yield the title compound as a clear, colorless oil (7.2 g, 100%) which was used without further purification. MH+199.

Preparation 53

1-(Benzyloxyimino-Methyl)-3-Butyl-Cyclobutanecarboxylic Acid Methyl Ester

A mixture of 3-butyl-1-formyl-cyclobutanecarboxylic acid methyl ester (7.2 g, 36.7 mmol), sodium acetate (6.1 g, 73.4 mmol) and O-benzylhydroxylamine hydrochloride (11.9 g, 73.4 mmol) were stirred in methanol (90 mL) for 18 h. The methanol was removed in vacuo, water (100 mL) was added and the aqueous phase was extracted with EtOAc (75 mL×5). The combined organic extracts were dried (MgSO$_4$) and were evaporated in vacuo. The residue was purified by flash column chromatography using an eluting system of hexane/EtOAc (9:1) to yield the title compound as a clear colorless oil (7.23 g, 64%). MH+304.

Preparation 54

1-(Benzyloxyimino-Methyl)-3-Butyl-Cyclobutanecarboxylic Acid

A mixture of 1-(benzyloxyimino-methyl)-3-butyl-cyclobutanecarboxylic acid methyl ester (7.23 g, 23.8 mmol) and lithium hydroxide monohydrate (10 g, 238 mmol) in THF (100 mL) and water (50 mL) was heated at 90° C. for 18 h. The reaction mixture was acidified to pH 3 with 6N aqueous HCl and was extracted with dichloromethane (75 mL×6). The combined organic layers were dried (MgSO$_4$) and were evaporated in vacuo to yield the title compound as a pale yellow oil. (6.33 g, 92%). MH+290.

Preparation 55

1-(Benzyloxyamino-Methyl)-3-Butyl-Cyclobutanecarboxylic Acid

A solution of 1-(benzyloxyimino-methyl)-3-butyl-cyclobutanecarboxylic acid (5.62 g, 19.4 mmol) in methanol (200 mL) at 0° C. under a nitrogen atmosphere was added a trace amount of methyl orange. A solution of saturated methanolic HCl was added until a persistent red color was observed. Sodium cyanoborohydride (1.59 g, 25.3 mmol) was added portionwise alternately with methanolic HCl to maintain the red color. The reaction mixture was maintained at 0° C. for an additional 0.5 h and the volatiles were removed in vacuo. The product was used without further purification. MH+292.

Preparation 56

1-[(Benzyloxy-formyl-Amino)-Methyl)]-3-Butyl-Cyclobutanecarboxylic Acid

To a cold solution of formic acid (72.4 mL, 1.9 mol) in dichloromethane (250 mL) at 0° C. under a nitrogen atmosphere was added acetic anhydride (27.4 mL, 0.29 mol). After 0.5 h, a solution of 1-(benzyloxyamino-methyl)-3-butyl-cyclobutanecarboxylic acid (5.65 g, 19.5 mmol) in dichloromethane (150 mL) was added. The reaction was stirred at room temperature for 3 h and was concentrated in vacuo. Water (200 mL) was added and the mixture was extracted with dichloromethane (75 mL×6). The combined organic extracts were dried (MgSO$_4$) and were evaporated in vacuo to yield the title compound as a white wax (1.59 g, 97%). MH+320.

Preparation 57

N-Benzyloxy-N-{3-Butyl-1-[N'-(4-Trifluoromethyl-Pyrimidin-2-yl)-Hydrazinocarbonyl]-Cyclobutylmethyl}-Formamide To a mixture of (1-[(benzyloxy-formyl-amino)-methyl)]-3-butyl-cyclobutanecarboxylic acid (0.10 g, 0.31 mmol), 2-hydrazino-4-(trifluoromethyl)pyrimidine (0.067 g, 0.37 mmol), NMM (0.095 g, 0.93 mmol) and HOAt (0.05 g, 0.37 mmol) in DMF (3 mL) at room temperature was added 1-[3-(dimethylamino)-propyl]-3-ethylcarbodiimide hydrochloride (0.072 g, 0.37 mmol). After stirring at room temperature 18 h, the reaction mixture was then purified by preparative, reverse-phase HPLC to afford the title compound as a white solid (0.07 g, 47%). MH+480.

Preparation 58

4-Ethyl-Cyclohexanecarboxylic Acid Methyl Ester

4-Ethyl-cyclohexanecarboxylic acid (9.8 g, 62.8 mmol) was stirred in saturated methanolic HCl (100 mL) at 45° C. for 18 h. The reaction micture was evaporated to provide the title compound as a clear colorless liquid (10.4 g, 98%). MH+171.

Preparation 59

4-Ethyl-Cyclohexane-1,1-Dicarboxylic Acid Dimethyl Ester

A solution of 4-ethyl-cyclohexanecarboxylic acid methyl ester (10.4 g, 61.2 mmol) in THF (25 mL) was added dropwise to a solution of lithium diisopropylamine (11.2 g, 92 mmol) in THF (90 mL) at −78° C. After stirring for 1 h at the same temperature, a solution of methylchloroformate (8.7 g, 92 mmol) in THF (25 mL) was added slowly and the mixture was allowed to warm to room temperature. After 18 h the reaction mixture was quenched with saturated aqueous NH$_4$Cl solution (150 mL). THF was removed in vacuo and the aqueous residue was extracted with EtOAc (200 mL×3). The combined organic layers were dried (MgSO$_4$). After removal of the solvent under reduced pressure, purification by flash column chromatography using an eluting system of hexane/EtOAc (95:5) yielded the title compound as a colorless liquid (14 g) with diisopropyl-carbamic acid methyl ester present. MH+229.

Preparation 60 cis-4-Ethyl-1-Formyl-Cyclohexanecarboxylic Acid Methyl Ester

To a solution of 4-ethyl-cyclohexane-1,1-dicarboxylic acid dimethyl ester (13 g, 57 mmol) in ether (400 mL) at −78° C. under a nitrogen atmosphere was added diisobutylaluminum hydride (1.5M in toluene, 76 mL, 114 mmol) dropwise. After 2 h, the reaction mixture was quenched with saturated aqueous NH$_4$Cl solution (130 mL), then 1N HCl (130 mL) and allowed to warm to room temperature. The mixture was filtered through Celite@ and the organic phase was separated, was dried (MgSO4) and was evaporated in vacuo to yield the title compound which was used without further purification. MH+199.

Preparation 61 cis-1-(Benzyloxyimino-Methyl)-4-Ethyl-Cyclohexanecarboxylic Acid Methyl Ester A mixture of cis-4-ethyl-1-formyl-cyclohexanecarboxylic acid methyl ester (57 mmol, theoretical from Preparation 60), sodium acetate (9.35 g, 114 mmol) and O-benzylhydroxylamine hydrochloride (18.2 g, 114 mmol) were stirred in methanol (200 mL) for 18 h. The methanol was removed in vacuo and the residue purified by flash column chromatography using an eluting system of hexane/EtOAc (9:1) to yield the title compound as a colorless oil (10.25 g, 60%). MH+304.

Preparation 62 cis-1-(Benzyloxyimino-Methyl)-4-Ethyl-Cyclohexanecarboxylic Acid

A mixture of cis-1-(benzyloxyimino-methyl)-4-ethyl-cyclohexanecarboxylic acid methyl ester (10.25 g, 33.8 mmol) and lithium hydroxide monohydrate (14.2 g, 0.34 mol) in THF (100 mL) and water (35 mL) was stirred at 65° C. for 18 h. The reaction mixture was acidified to pH 6 with 3N aqueous HCl and was extracted with DCM (100 mL×2). The combined organic layers were dried (MgSO$_4$) and were evaporated in vacuo to yield the title compound as a pale yellow oil (8.43 g, 86%). MH+290.

Preparation 63 cis-1-(Benzyloxyamino-Methyl)-4-Ethyl-Cyclohexanecarboxylic Acid

To a solution of cis-1-(benzyloxyimino-methyl)-4-ethyl-cyclohexanecarboxylic acid (8.43 g, 29.2 mmol) in methanol (200 mL) at 0° C. under a nitrogen atmosphere was added a trace amount of methyl orange. A solution of saturated methanolic HCl was added until a persistent red color was observed. Sodium cyanoborohydride (2.2 g, 35 mmol) was added portionwise alternately with methanolic HCl to maintain the red color. The reaction mixture was maintained at 0° C. for an additional 2 h and the volatiles were removed in vacuo to yield the title compound as a gummy soild that was used without further purification. MH+292.

Preparation 64 cis-1-[(Benzyloxy-Formyl-Amino)-Methyl]-4-Ethyl-Cyclohexanecarboxylic Acid

To a cold solution of formic acid (72 mL, 1.9 mol) in dichloromethane (200 mL) at 0° C. under a nitrogen atmosphere was added acetic anhydride (27 mL, 290 mmol). After 1 h, a solution of cis-1-(benzyloxyamino-methyl)-4-ethyl-cyclohexanecarboxylic acid from Preparation 63 (29 mmol theoretical) in dichloromethane (200 mL) was added. The mixture was stirred at room temperature for 1 h and was concentrated in vacuo. Water (200 mL) was added, the organic layer was separated, was dried (MgSO$_4$) and was evaporated in vacuo to yield the title compound as a white solid (8.25 g, 89%). MH+320.

Preparation 65 cis-N-Benzyloxy-N-{4-Ethyl-1-[N'-(4-Trifluoromethyl-Pyrimidin-2-yl)-Hydrazinocarbonyl]-Cyclohexylmethyl}-Formamide To a mixture of cis-1-[(benzyloxy-formyl-amino)-methyl]4-ethyl-cyclohexanecarboxylic acid (0.1 g, 0.31 mmol), 2-hydrazino-4-(trifluoromethyl)pyrimidine (0.068 g, 0.37 mmol), NMM (0.095 g, 0.93 mmol) and HOAt (0.05 g, 0.37 mmol) in DMF (1 mL) at room temperature was added 1-[3-(dimethylamino)-propyl]-3-ethylcarbodiimide hydrochloride (0.073 g, 0.37 mmol). After stirring at room temperature 18 h, the reaction mixture was then purified by preparative, reverse-phase HPLC to afford the title compound as a white solid (0.088 g, 59%). MH+480.

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214 nm, and a light scattering detector (ELS). Column: 1×40 mm Aquasil (C18).

The following synthetic schemes are merely illustrative of the methods by which the compounds of the invention may be prepared and are not intended to limit the scope of the invention as defined in the appended claims.

The compounds disclosed in Examples 2 to 32 were prepared following the general procedures described in Example 1.

Example 1

N-Hydroxy-N-{cis-4-Methyl-1-[N'-(4-Trifluoromethyl-Pyrimidin-2-yl)-hydrazinocarbonyl]-Cyclohexylmethyl}-Formamide To a solution of N-benzyloxy-N-{cis-4-methyl-1[N'-(4-triflouromethyl-pyrimidin2-yl)-hydrazinocarbonyl]-cyclohexylmethyl}-formamide (0.07 g, 0.15 mmol) in methanol (5 mL) was added 10% Pd/C (0.015 g). The reaction mixture was subjected to hydrogenation for 4 h at room temperature. The reaction mixture was then filtered through a pad of Celite@, and washed with methanol (20 mL). Removal of the solvent provided the title compound as a white solid (0.05 g, 86%). MH+376.

Example 2

N-Hydroxy-N-{Cis-4-Methyl-1-[N'-(4-Methyl-Pyrimidin-2-yl)-hydrazinocarbonyl]-Cyclohexylmethyl}-Formamide

MH+322.

Example 3

N-Hydroxy-N-{Cis-4-Methyl-1-[N'-(4-Morpholin-4-yl-6-Trifluoromethyl-Pyrimidin-2-yl)-Hydrazinocarbonyl]-Cyclohexylmethyl}-Formamide

MH+461.

Example 4

N-Hydroxy-N-{Cis-4-Methyl-1-[N'-(7-Methyl-Benzo[1,2,4]Triazin-3-yl)-Hydrazinocarbonyl]-Cyclohexylmethyl}-Formamide

MH+373.

Example 5

N-Hydroxy-N-{Cis-4-Methyl-1-[N'-(5-Methyl-Benzo[1,2,4]Triazin-3-yl)-Hydrazinocarbonyl]-Cyclohexylmethyl}-Formamide

MH+373.

Example 6

N-Hydroxy-N-{Cis-4-Methyl-1-[N'-(5,7-Dimethyl-Benzo[1,2,4]Triazin-3-yl)-Hydrazinocarbonyl]-Cyclohexylmethyl}-Formamide

MH+387.

Example 7

Benzofuran-2-Carboxylic Acid {[(Cis-1-{1-[(Formyl-Hydroxy-Amino)-Methyl]-4-Methyl-Cyclohexyl}-Methanoyl)-Amino]-Methyl}-Amide

MH+388.

Example 8

N-Hydroxy-N-(Cis-1-{N'-[1-(7-Methoxy-Benzofuran-2-yl)-Methanoyl]-Hydrazinocarbonyl}-4-Methyl-Cyclohexylmethyl)-Formamide

MH+404.

Example 9

N-Hydroxy-N-{1-[N'-(4-Trifluoromethyl-Pyrimidin-2-yl)-Hydrazinocarbonyl]-Cyclopentylmethyl}-Formamide To a solution of N-benzyloxy-N-{1-[N'-(4-trifluoromethyl-pyrimidin-2-yl)-hydrazinocarbonyl]-cyclopentylmethyl}-formamide (0.085 g, 0.19 mmol) in methanol (10 mL) was added 10% Pd/C (0.03 g). The reaction mixture was subjected to hydrogenation for 4 h at room temperature. The reaction mixture was then filtered through a pad of Celite@, and washed with methanol (20 mL). Removal of the solvent provided the title compound as a white solid (0.025 g, 38%). MH+348.

Example 10

N-Hydroxy-N-{1-[N'-(7-Methoxy-Benzofuran-2-Carbonyl)-Hydrazinocarbonyl]-Cyclopentylmethyl}-Formamide

MH+376.

Example 11

N-Hydroxy-N-{1-[N'-(4-Trifluoromethyl-Pyrimidin-2-yl)-Hydrazinocarbonyl]-Cyclohexylmethyl}-Formamide To a solution of N-benzyloxy-N-{1-[N'-(4-trifluoromethyl-pyrimidin-2-yl)-hydrazinocarbonyl]-cyclohexylmethyl}-formamide (0.066 g, 0.15 mmol) in ethanol (5 mL) was added 10% Pd/C (0.03 g). The reaction mixture was subjected to hydrogenation for 3 h at room temperature. The reaction mixture was then filtered through a pad of Celite@, and washed with ethanol (20 mL). Removal of the solvent provided the title compound as a white solid (0.045 g, 85%). MH+362.

Example 12

N-Hydroxy-N-{1-[N'-(7-Methoxy-Benzofuran-2-Carbonyl)-Hydrazinocarbonyl]-Cyclohexylmethyl}-Formamide

MH+390.

Example 13

N-Hydroxy-N-{1-[N'-(5-Methoxy-Benzo[1,2,4Triazin-3-yl)-Hydrazinocarbonyl]-Cyclohexylmethyl}-Formamide

MH+375.

Example 14

N-Hydroxy-N-{1-[N'-(7-Methyl-Benzo[1,2,4Triazin-3-yl)-Hydrazinocarbonyl]-Cyclohexylmethyl}-Formamide

MH+359.

Example 15

N-{4,4-Dimethyl-1-[N'-(4-Trifluoromethyl-Pyrimidin-2-yl)-Hydrazinocarbonyl]-Cyclohexylmethyl}-N-Hydroxy-Formamide To a solution of N-benzyloxy-N-{4,4-dimethyl-1-[N'-(4-trifluoromethyl-pyrimidin2-yl)-hydrazinocarbonyl]-cyclohexylmethyl}-formamide (0.11 g, 0.23 mmol) in methanol (10 mL) was added 10% Pd/C (0.032 g). The reaction mixture was subjected to hydrogenation for 1 h at room temperature. The reaction mixture was then filtered through a pad of Celite@, and washed with methanol (20 mL). Removal of the solvent provided the title compound as a white solid (0.066 g, 74%). MH+390.

Example 16

N-{4,4-Dimethyl-1-[N'-(4-Methyl-Pyrimidin-2-yl)-Hydrazinocarbonyl]-Cyclohexylmethyl}-N-Hydroxy-Formamide

MH+336

Example 17

N-{4,4-Dimethyl-1-[N'-(4-Methyl-6-Morpholin-4-yl-Pyrimidin-2-yl)-Hydrazinocarbonyl]-Cyclohexylmethyl}-N-Hydroxy-Formamide

MH+421

Example 18

N-{4,4-Dimethyl-1-[N'-(4-Trifluoromethyl-6-Morpholin-4-yl-Pyrimidin-2-yl)-Hydrazinocarbonyl]-Cyclohexylmethyl}-N-Hydroxy-Formamide

MH+475

Example 19

N-{4,4-Dimethyl-1-[N'-(7-Methyl-Benzo[1,2,4]Triazin-3-yl)-Hydrazinocarbonyl]-Cyclohexylmethyl}-N-Hydroxy-Formamide

MH+387

Example 20

N-{4,4-Dimethyl-1-[N'-(5-Methyl-Benzo[1,2,4]Triazin-3-yl)-Hydrazinocarbonyl]Formamide

MH+387

Example 21

N-{4,4-Dimethyl-1-[N'-(4-Methyl-Pyridin-2-yl)-Hydrazinocarbonyl]-Cyclohexylmethyl}-N-Hydroxy-Formamide

MH+387

Example 22

N-{1-[N'-(Dimethylamino-Ethyl-[1,3,5]Triazin-2-yl)-Hydrazinocarbonyl]-4,4-Dimethyl-Cyclohexylmethyl}-N-Hydroxy-Formamide

MH+394

Example 23

Benzofuran-2-Carboxylic Acid {[(1-{-[(Formyl-Hydroxy-Amino)-Methyl]-4,4-Dimethyl-Cyclohexyl}-Methanoyl)-Amino]-Methyl}-Amide

MH+402

Example 24

N-Hydroxy-N-{1-[N'-(4-Trifluoromethyl-Pyrimidin-2-yl)-Hydrazinocarbonyl]-Cycloheptylmethyl}-Formamide To a solution of N-benzyloxy-N-{1-[N'-(4-trifluoromethyl-pyrimidin-2-yl)-hydrazinocarbonyl]-cycloheptylmethyl}-formamide (0.11 g, 0.24 mmol) in methanol (10 mL) was added 10% Pd/C (0.03 g). The reaction mixture was subjected to hydrogenation for, 0.25 h at room temperature. The reaction mixture was then filtered through a pad of Celite@, and washed with methanol (20 mL). Removal of the solvent provided the title compound as a white solid (0.067 g, 75%). MH+376.

Example 25

N-Hydroxy-N-{1-[N'-(4-Methyl-Pyrimidin-2-yl)-Hydrazinocarbonyl]-Cycloheptylmethyl}-Formamide

MH+322

Example 26

N-Hydroxy-N-{1-[N'-(4-Methyl-6-Morpholin-4-yl-Pyrimidin-2-yl)-Hydrazinocarbonyl]-Cycloheptylmethyl}-Formamide

MH+407

Example 27

N-(1-{1N'-[4-(4-Ethyl-Piperazin-1-yl)-6-Methyl-Pyrimidin-2-yl]-Hydrazinocarbonyl}-Cycloheptylmethyl)-N-Hydroxy-formamide

MH+434

Example 28

N-Hydroxy-N-{1-[N'-(4-Methyl-Pyridin-2-yl)-Hydrazinocarbonyl]-Cycloheptylmethyl}-Formamide

MH+321

Example 29

N-Hydroxy-N-{1-[N'-(5-Methyl-Benzo[1,2,4]Triazin-3-yl)-Hydrazinocarbonyl]-Cycloheptylmethyl}-Formamide

MH+373

Example 30

N-Hydroxy-N-{1-[N'-(7-Methyl-Benzo[1,2,4]Triazin-3-yl)-Hydrazinocarbonyl]-Cycloheptylmethyl}-Formamide

MH+373

Example 31

N-Hydroxy-N-{1-[N'-(7-Methoxy-Benzofuran-2-Carbonyl)-Hydrazinocarbonyl]-Cycloheptylmethyl}-Formamide

MH+404

Example 32

Benzofuran-2-Carboxylic Acid {[(1-{-[(Formyl-Hydroxy-Amino)-Methyl]-Cycloheptyl}-Methanoyl)-Amino]-Methyl}-Amide

MH+388

Example 33

N-{(3S,5R)-3,5-Dimethyl-1-[N'-(4-Trifluoromethyl-Pyrimidin-2-yl)-Hydrazinocarbonyl]-Cyclohexylmethyl}-N-Hydroxy-Formamide To a solution of N-Benzyloxy-N-{(3S,5R)-3,5-dimethyl-1-[N'-(4-trifluoromethyl-pyrimidin-2-yl)-hydrazinocarbonyl]-cyclohexylmethyl}-formamide (0.09 g, 0.19 mmol) in methanol (10 mL) was added 10% Pd/C (0.028 g). The reaction mixture was subjected to hydrogenation for 1 h at room temperature. The reaction mixture was then filtered through a pad of Celite@, and washed with methanol (20 mL). Removal of the solvent provided the title compound as a beige solid (0.053 g, 73%). MH+390.

Example 34

N-{(3S,5R)-3,5-Dimethyl-1-[N'-(4-Methyl-Pyrimidin-2-yl)-Hydrazinocarbonyl]-Cyclohexylmethyl}-N-Hydroxy-Formamide

MH+336

Example 35

N-{(3S,5R)-3,5-Dimethyl-1-[N'-(7-Methyl-Benzo[1,2,4]Triazin-3-yl)-Hydrazinocarbonyl]-Cyclohexylmethyl}-N-Hydroxy-Formamide

MH+387

Example 36

N-{(3S,5R)-3,5-Dimethyl-1-[N'-(4-Methyl-Pyridin-2-yl)-Hydrazinocarbonyl]-Cyclohexylmethyl}-N-Hydroxy-Formamide

MH+335

Example 37

N-{(3S,5R)-1-[N'-(Dimethylamino-Ethyl-[1,3,5]
Triazin-2-yl)-Hydrazinocarbonyl]-3,5-Dimethyl-
Cyclohexylmethyl}-N-Hydroxy-Formamide

MH+394

Example 38

N-{3-Butyl-1-[N'-(4-Trifluoromethyl-Pyrimidin-2-
yl)-Hydrazinocarbonyl]-Cyclobutylmethyl}-N-Hy-
droxy-Formamide To a solution of N-benzyloxy-N-{3-butyl-1-[N'-(4-trifluo-romethyl-pyrimidin-2-yl)-hydrazinocarbonyl]-cyclobutylmethyl}-formamide (0.07 g, 0.15 mmol) in methanol (10 mL) was added 10% Pd/C (0.02 g). The reaction mixture was subjected to hydrogenation for 4 h at room temperature. The reaction mixture was then filtered through a pad of Celite@, and washed with methanol (20 mL). Removal of the solvent provided the title compound as a beige solid (0.042 g, 73%). MH+390.

Example 39

N-{3-Butyl-1-[N'-(7-Methyl-Benzo[1,2,4]Triazin-3-
yl)-Hydrazinocarbonyl]-Cyclobutylmethyl}-N-Hy-
droxy-Formamide

MH+387

Example 40

N-{3-Butyl-1-[N'-(4-Methyl-Pyridin-2-yl)-Hydrazi-
nocarbonyl]-Cyclobutylmethyl}-N-Hydroxy-Forma-
mide

MH+335

Example 41

N-{3-Butyl-1-[N'-(Dimethylamino-Ethyl-[1,3,5]
Triazin-2-yl)-Hydrazinocarbonyl]-Cyclobutylm-
ethyl}-N-Hydroxy-Formamide

MH+394

Example 42

N-{3-Butyl-1-[N'-(4-Methyl-Pyrimidin-2-yl)-Hy-
drazinocarbonyl]-Cyclobutylmethyl}-N-Hydroxy-
formamide

MH+336

Example 43

N-{3-Butyl-1-[N'-(4-Pyridin-2-yl-Pyrimidin-2-yl)-
Hydrazinocarbonyl]-Cyclobutylmethyl}-N-Hy-
droxy-formamide

MH+399

Example 44

Cis-N-{4-ethyl-1-[N'-(4-Trifluoromethyl-Pyrimidin-
2-yl)-Hydrazinocarbonyl]-Cyclohexylmethyl}-N-
Hydroxy-Formamide To a solution of cis-N-benzyloxy-N-{4-ethyl-1-[N'-(4-trif-luoromethyl-pyrimidin-2-yl)-hydrazinocarbonyl]-cyclo-hexylmethyl-formamide (0.088 g, 0.18 mmol) in methanol (5 mL) was added 10% Pd/C (0.008 g). The reaction mixture was subjected to balloon hydrogenation for 1 h at room temperature. The reaction mixture was then filtered through a pad of Celite@, and washed with methanol (20 mL). Removal of the solvent provided the title compound as a white solid (0.055 g, 77%). MH+390.

Example 45

Cis-N-{4-Ethyl1-1-[N'-(4-Methyl-Pyrimidin-2-yl)-
Hydrazinocarbonyl]-Cyclohexylmethyl}-N-Hy-
droxy-Formamide

MH+336.

Example 46

Cis-N-{4-Ethy1-1-[N'-(7-Methyl-Benzo[1,2,4]Tri-
azin-3-yl)-Hydrazinocarbonyl]-Cyclohexylmethyl}-
N-Hydroxy-Formamide

MH+387.

Example 47

Cis-N-{4-Ethy1-1-[N'-(4-Methyl-Pyridin-3-yl)-Hy-
drazinocarbonyl]-Cyclohexylmethyl}-N-Hydroxy-
Formamide

MH+335.

Example 48

Cis-N-{1-[N'-(Dimethylamino-Ethyl-[1,3,5]Triazin-
2-yl)-Hydrazinocarbonyl]-4-Ethyl-Cyclohexylm-
ethyl}-N-Hydroxy-formamide

MH+394.

The following examples were prepared by the same methods of Example 1.

Example 49

Cis-N-(1-{N'-[4-(2-Amino-Phenyl)-Pyrimidin-2-yl]-
Hydrazinocarbonyl}-4-Methyl-Cyclohexylmethyl}-
N-Hydroxy-formamide

MH+399.

Example 50

Cis-N-{1-[N'-(4-Furan-3-yl-Pyrimidin-2-yl)-Hydrazinocarbonyl]-4-Methyl-Cyclohexylmethyl}-N-Hydroxy-Formamide

MH+374.

Example 51

Cis-N-Hydroxy-N-{4-Methyl-1-[N'-(4-Pyridin-2-yl-Pyrimidin-2-yl)-Hydrazinocarbonyl]-Cyclohexylmethyl}-Formamide

MH+385.

Example 52

Cis-N-{1-[N'-(Dimethylamino-Ethyl-[1,3,5]Triazin-2-yl)-Hydrazinocarbonyl]-4-Methyl-Cyclohexylmethyl}-N-Hydroxy-Formamide

MH+380.

Example 53

Cis-N-{1-[N'-(4-Ethyl-6-Morpholin-4-yl-[1,3,5]Triazin-2-yl)-Hydrazinocarbonyl]-4-Methyl-Cyclohexylmethyl}-N-Hydroxy-formamide

MH+422.

Example 54 cis-N-{1-[N'-(3,6-Dimethyl-Pyrazin-2-yl)-Hydrazinocarbonyl]-4-Methyl-Cyclohexylmethyl}-N-Hydroxy-formamide

MH+336.

Example 55

Cis-N-{1-[N'-(6-Chloro-Pyrazin-2-yl)-Hydrazinocarbonyl]-4-Methyl-Cyclohexylmethyl}-N-Hydroxy-Formamide

MH+342/344.

Example 56 cis-N-Hydroxy-N [4-Methyl-1-(N'-Pyrazin-2-yl-Hydrazinocarbonyl)-Cyclohexylmethyl]-Formamide

MH+308.

Example 57

Cis-N-Hydroxy-N {4-Methyl-1-(N'-(6-Morpholin-4-yl-Pyrazin-2-yl)-Hydrazinocarbonyl)-Cyclohexylmethyl}-formamide

MH+393.

Example 58

Cis-N-{1-[N'-(6-Furan-2-yl-Pyrazin-2-yl)-Hydrazinocarbonyl]-4-Methyl-Cyclohexylmethyl}-N-Hydroxy-Formamide

MH+374.

Example 59 cis-N-{1-[N'-(Dimethylamino-Methyl-Pyrimidin-2-yl)-Hydrazinocarbonyl]-4-Methyl-Cyclohexylmethyl}-N-Hydroxy-Formamide

MH+365.

Example 60

Cis-N-(1-{N'-[4-(Ethyl-Piperazin-1-yl)-6-Methyl-Pyrimidin-2-yl]-Hydrazinocarbonyl}-4-Methyl-Cyclohexylmethyl)-N-Hydroxy-Formamide

MH+434.

Example 61

Cis-N-{1-[N'-(4-Cyclopropyl-6-Pyridin-2-yl-Pyrimidin-2-yl)-Hydrazinocarbonyl]-4-Methyl-Cyclohexylmethyl}-N-Hydroxy-formamide

MH+425.

Example 62

Cis-N-Hydroxy-N-{4-Methyl-1-[N'-(4-Methyl-6-Morpholin-4-yl-Pyrimidin-2-yl)-hydrazinocarbonyl]-Cyclohexylmethyl}-formamide

MH+407.

Example 63

Cis-N-Hydroxy-N-{4-Methyl-1-[N'-(4-Pyridin-3-yl-Pyrimidin-2-yl)-Hydrazinocarbonyl]-Cyclohexylmethyl}-Formamide

MH+385.

Compositions, Administration and Biological Assays

Compounds of Formula (1) and their pharmaceutically acceptable salts may be administered in a standard manner for antibiotics, for example orally, parenterally, sublingually, dermally, transdermally, rectally, via inhalation or via buccal administration. Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose. Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

S. aureus or E. coli PDF activity is measured at 25° C., using a continuous enzyme-linked assay developed by Lazennec & Meinnel ("Formate dehydrogenase-coupled spectrophotometric assay of peptide deformylase", Anal. Biochem. 1997, 244, pp. 180-182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (1):

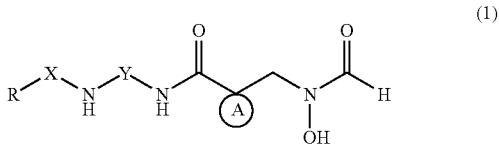

wherein:

A is an optionally substituted 3 to 8 membered carbocycle ring;

Y is a bond except when X is carbonyl Y is a bond or $CH_2$;

X is a carbonyl, $CH_2$ or a bond;

R is selected from the group consisting of aryl and heteroaryl; or a pharmaceutically acceptable salt thereof.

2. A compound according to claim 1 selected from the group consisting of:

N-Hydroxy-N-{cis-4-methyl-1-[N'-(4-trifluoromethyl-pyrimidin-2-yl)-hydrazinocarbonyl]-cyclohexylmethyl}-formamide;

N-Hydroxy-N-{cis-4-methyl-1-[N'-(4-methyl-pyrimidin-2-yl)-hydrazinocarbonyl]-cyclohexylmethyl}-formamide;

N-Hydroxy-N-{cis-4-methyl-1-[N'-(4-morpholin-4-yl-6-trifluoromethyl-pyrimidin-2-yl) -hydrazinocarbonyl]-cyclohexylmethyl}-formamide;

N-Hydroxy-N-{cis-4-methyl-1-[N'-(7-methyl-benzo[1,2,4]triazin-3-yl)-hydrazinocarbonyl]-cyclohexylmethyl}-formamide;

N-Hydroxy-N-{cis-4-methyl-1-[N'-(5-methyl-benzo[1,2,4]triazin-3-yl)-hydrazinocarbonyl]-cyclohexylmethyl}-formamide;

N-Hydroxy-N-{cis-4-methyl-1-[N'-(5,7-dimethyl-benzo[1,2,4]triazin-3-yl)-hydrazinocarbonyl]-cyclohexylmethyl}-formamide;

Benzofuran-2-carboxylic acid {[(cis-1-{1-](formyl-hydroxy-amino)-methyl]-4-methyl-cyclohexyl}-methanoyl)-amino]-methyl}-amide;

N-Hydroxy-N-(cis-1-{N'-[1-(7-methoxy-benzofuran-2-yl)-methanoyl]-hydrazinocarbonyl}-4-methyl-cyclohexylmethyl)-formamide;

N-Hydroxy-N-{1-[N'-(4-trifluoromethyl-pyrimidin-2-yl)-hydrazinocarbonyl]-cyclopentylmethyl}-formamide;

N-Hydroxy-N-{1-[N'-(7-methoxy-benzofuran-2-carbonyl)-hydrazinocarbonyl]-cyclopentylmethyl}-formamide;

N-Hydroxy-N-{1-[N'-(4-trifluoromethyl-pyrimidin-2-yl)-hydrazinocarbonyl]-cyclohexylmethyl}-formamide;

N-Hydroxy-N-{1-[N'-(7-methoxy-benzofuran-2-carbonyl)-hydrazinocarbonyl]-cyclohexylmethyl}-formamide;

N-Hydroxy-N-{1-[N'-(5-methoxy-benzo[1,2,4triazin-3-yl)-hydrazinocarbonyl]-cyclohexylmethyl}-formamide;

N-Hydroxy-N-{1-[N'-(7-methyl-benzo[1,2,4triazin-3-yl)-hydrazinocarbonyl]-cyclohexylmethyl}-formamide;

N-{4,4-Dimethyl-1-[N'-(4-trifluoromethyl-pyrimidin-2-yl)-hydrazinocarbonyl]-cyclohexylmethyl}-N-hydroxy-formamide;

N-{4,4-Dimethyl-1-[N'-(4-methyl-pyrimidin-2-yl)-hydrazinocarbonyl]-cyclohexylmethyl}-N-hydroxy-formamide;

N-{4,4-Dimethyl-1-[N'-(4-methyl-6-morpholin-4-yl-pyrimidin-2-yl)-hydrazinocarbonyl]-cyclohexylmethyl}-N-hydroxy-formamide;

N-{4,4-Dimethyl-1-[N'-(4-trifluoromethyl-6-morpholin-4-yl-pyrimidin-2-yl)-hydrazinocarbonyl]-cyclohexylmethyl}-N-hydroxy-formamide;

N-{4,4-Dimethyl-1-[N'-(7-methyl-benzo[1,2,4]triazin-3-yl)-hydrazinocarbonyl]-cyclohexylmethyl}-N-hydroxy-formamide;

N-{4,4-Dimethyl-1-[N'-(5-methyl-benzo[1,2,4]triazin-3-yl)-hydrazinocarbonyl]-cyclohexylmethyl}-N-hydroxy-formamide;

N-{4,4-Dimethyl-1-[N'-(4-methyl-pyridin-2-yl)-hydrazinocarbonyl]-cyclohexylmethyl}-N-hydroxy-formamide;

N-{1-[N'-(Dimethylamino-ethyl-[1,3,5]triazin-2-yl)-hydrazinocarbonyl]-4,4-dimethyl-cyclohexylmethyl}-N-hydroxy-formamide;

Benzofuran-2-carboxylic acid {[(1-{-[(formyl-hydroxy-amino)-methyl]-4,4-dimethyl-cyclohexyl}-methanoyl)-amino]-methyl}-amide;

N-Hydroxy-N-{1-[N'-(4-trifluoromethyl-pyrimidin-2-yl)-hydrazinocarbonyl]-cycloheptylmethyl}-formamide;

N-Hydroxy-N-{1-[N'-(4-methyl-pyrimidin-2-yl)-hydrazinocarbonyl]-cycloheptylmethyl}-formamide;

N-Hydroxy-N-{1-[N'-(4-methyl-6-morpholin-4-yl-pyrimidin-2-yl)-hydrazinocarbonyl]-cycloheptylmethyl}-formamide;

N-(1-{N'-A[4-(4-Lthyl-piperazin-1-yl)-6-methyl-pyrimidin-2-yl]-hydrazinocarbonyl}-cycloheptylmethyl)-N-hydroxy-formamide;

N-Hydroxy-N-{1-[N'-(4-methyl-pyridin-2-yl)-hydrazinocarbonyl]-cycloheptylmethyl}-formamide;

N-Hydroxy-N-{1-[N'-(5-methyl-benzo[1,2,4]triazin-3-yl)-hydrazinocarbonyl]-cycloheptylmethyl}-formamide;

N-Hydroxy-N-{1-[N'-(7-methyl-benzo[1,2,4]triazin-3-yl)-hydrazinocarbonyl]-cycloheptylmethyl}-formamide;

N-Hydroxy-N-{1-[N'-(7-methoxy-benzofuran-2-carbonyl)-hydrazinocarbonyl]-cycloheptylmethyl}-formamide; and Benzofuran-2-carboxylic acid {[(1-{-[(formyl-hydroxy-amino)-methyl]-cycloheptyl}-methanoyl)-amino]-methyl}-amide; or a pharmaceutically acceptable salt thereof.

3. A pharmaceutical composition comprising a compound according to claim 1, or a pharmaceutically acceptable salt thereof, and a pharmaceutically acceptable carrier.

* * * * *